United States Patent [19]
Junius-Comer et al.

[11] Patent Number: 5,204,242
[45] Date of Patent: Apr. 20, 1993

[54] SUBSTITUTED PHENOLS

[75] Inventors: Martina Junius-Comer, Iffeldorf; Bernd Vogt, Tutzing; Rupert Herrmann, Weilheim, all of Fed. Rep. of Germany

[73] Assignee: Boehringer Mannheim GmbH, Mannheim-Waldhof, Fed. Rep. of Germany

[21] Appl. No.: 761,335

[22] Filed: Sep. 17, 1991

[30] Foreign Application Priority Data
Sep. 19, 1990 [DE] Fed. Rep. of Germany ....... 4029709

[51] Int. Cl.$^5$ .......................... G03C 1/06; G03C 1/40; C07C 79/32
[52] U.S. Cl. ...................... 435/28; 568/709; 560/254; 430/364; 430/365; 430/566
[58] Field of Search .......................... 435/28; 568/709; 560/254; 430/364, 365, 566

[56] References Cited

U.S. PATENT DOCUMENTS

| | | | |
|---|---|---|---|
| 4,200,466 | 4/1980 | Fujiwhara et al. ................. | 430/566 |
| 4,387,158 | 6/1983 | Postle .................................... | 430/364 |
| 4,588,835 | 5/1986 | Torii et al. ............................ | 560/254 |
| 4,670,608 | 6/1987 | Paetz et al. .......................... | 568/709 |

FOREIGN PATENT DOCUMENTS

| | | |
|---|---|---|
| 0071569 | 2/1983 | European Pat. Off. . |
| 0108526 | 5/1984 | European Pat. Off. . |
| 0175151 | 3/1986 | European Pat. Off. . |
| 2644194 | 4/1977 | Fed. Rep. of Germany . |

OTHER PUBLICATIONS

Krohn, Chemical Abstracts, (1976) vol. 84, No. 17, 121383v.
Gibson et al., Chemical Abstracts, (1966) vol. 65, No. 3, p. 3783b.

Primary Examiner—Ronald W. Griffin
Assistant Examiner—Louise N. Leary
Attorney, Agent, or Firm—Felfe & Lynch

[57] ABSTRACT

The present invention provides a colorimetric process for the detection of an oxidative coupling reaction in which a coupling component is reacted with a developer component in the presence of an oxidation agent to give a colored material, wherein, as coupling component, there is used a compound of the general formula:

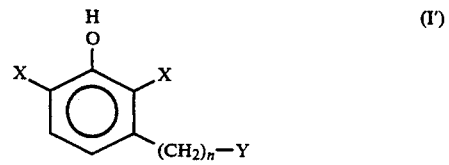

in which X is a bromine or chlorine atom, n is 1, 2 or 3, Y is COOR, CONRR', SO$_3$R, SO$_2$NRR', OR, NRR' or NRR'R''$\oplus$ and R, R' and R'', independently of one another, are hydrogen atoms or C$_1$–C$_3$-alkyl radicals.

The present invention also provides a reagent which contains the above compound, as well as new substituted phenols and a process for the preparation thereof.

39 Claims, No Drawings

SUBSTITUTED PHENOLS

The present invention is concerned with new substituted phenols, processes for the preparation thereof, colorimetric processes for the detection of an oxidative coupling reaction and reagents for the detection of an oxidative coupling reaction.

Not only for analytical chemistry but also for medical diagnosis, a detection process is of importance which is designated as an oxidative coupling. A coupling component is thereby reacted with a developer component in the presence of an oxidation agent to give a coloured material. The detection of hydrogen peroxide by means of appropriate chromogenic substances is of especially great importance. This applies especially for numerous detection processes in which hydrogen peroxide is formed as intermediate of the reaction of a substrate with an appropriate substrate oxidase and oxygen and is subsequently converted in the presence of appropriate chromogenic reaction components, preferably in the presence of a peroxidase (POD) as catalyst, into an optically detectable compound, i.e. into a coloured material, the amount of the resulting coloured material thereby being in quantitative relationship to the hydrogen peroxide formed. Furthermore, peroxidase is frequently used as enzyme label in immune tests and is detected by the addition of hydrogen peroxide and appropriate chromogenic reaction components.

In the case of the oxidative coupling reaction, a coupling component is reacted in the presence of a developer component to give a colored material. Numerous chromogenic or indicator systems have already been mentioned and employed for the detection of hydrogen peroxide/peroxidase. One of the best known ones is the indicator system described by Trinder (see Ann. Clin. Biochem., 6, 24/1969) hereby incorporated by reference in which phenol as coupling component is oxidatively coupled with 4-aminoantipyrine as developer component in the presence of peroxidase with the participation of hydrogen peroxide to give a colored material. 4-Aminoantipyrine as developer component can, for example, also be replaced by derivatives of aminoantipyrine, phenylenediamine or with methylbenzthiazoline hydrazone. Examples with methylbenzthiazoline hydrazone (MBTH) as developer have been described by N. Gochman et al. (Clin. Chem., 17, 1154/1971), T. T. Ngo et al. (Anal. Biochem., 105, 389/1980) and J. Siedel et al. (Anal. Lett., 21, 1009/1988) hereby incorporated by reference.

Furthermore, the oxidative coupling reaction can be used in order to determine aromatic amines liberated in the case of enzymatic reactions. Of especial importance for diagnostic purposes are the detection of γ-glutamyl-transpeptidase (γ-GT) and of leucinaminopeptidase (LAP), as well as of thrombin. In these cases, a "peptide amide", the amino acid sequence of which corresponds to the cleavage position of the enzyme in question and the amide moiety of which is an aromatic amine, especially phenylenediamine or aminophenol or a derivative thereof, which can serve as developer component of the oxidative coupling, is first cleaved by the enzyme and then oxidized with a coupling component by means of an oxidation agent to give a colored material (cf. published Federal Republic of Germany Patent Specification No. 33 31 588 and published European Patent Specification No. EP-A-0,076,042).

The sensitivity of the detection of the oxidative coupling reaction depends especially upon the coupling component used.

Various phenol derivatives have been described in the literature as coupling components for the oxidative coupling with which can be made available sensitive detection systems for hydrogen peroxide by condensation with developer components, for example 4-aminoantipyrine or substituted benzthiazolinone hydrazones (see J. Clin. Chem. Biochem., 15, 699/1977; Anal. Chim. Acta, 136, 121/1982; Anal. Lett., 21, 1009/1988; hereby incorporated by reference published European Patent Specification No. 0,108,526). The coloured materials resulting as coupling products display a high molar extinction coefficient which appears to be well suited for the detection of the oxidative coupling reaction. However, the high susceptibility to disturbance of these coupling products towards serum components, as well as the, in part, insufficient stability of the reaction components or of the coupling products, proves to be disadvantageous.

Phenol derivatives suitable for use as coupling components are described in published European Patent Specification No. EP-A-0,108,526. However, phenol derivatives there disclosed, for example, 2,4-dibromo-3-hydroxybenzoic acid, do not give reproducible results. Other phenolic couplers there disclosed, for example, 2,4,6-tribromo-3-hydroxybenzoic acid, have the disadvantage that the oxidative coupling is considerably disturbed by non-specific reducing substances in the serum or urine, for example bilirubin and ascorbic acid, and by pharmaceuticals, for example α-methyldopa and dobesilate calcium.

Thus, there is a great need for coupling components for oxidative coupling reactions in the case of which the disadvantages of the prior art, especially low stability and non-specific reactivity, are removed at least partially.

In published Federal Republic of Germany Patent Specification No. 23 20 967 (corresponding to issued U.S. Pat. Nos. 4,073,942 and 4,113,777 hereby incorporated by reference) are disclosed new benzylamines of the general formula:

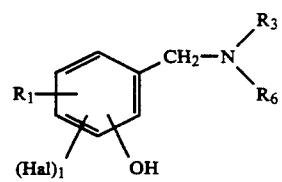

wherein $R_1$ is a hydrogen, chlorine or bromine atom, Hal is a chlorine or bromine atom, $R_3$ is a hydrogen atom or a methyl or ethyl radical, $R_6$ is a cyclohexyl, hydroxycyclohexyl or morpholinocarbonylmethyl radical and l is 1 or 2, and the physiologically acceptable salts thereof with organic and inorganic acids. To these compounds are attributed pharmacological properties, besides a promoting action on the production of the surfactant or antiatelectase factor and especially a secretolytic and anti-tussive action.

According to the present invention, there are provided compounds of the general formula:

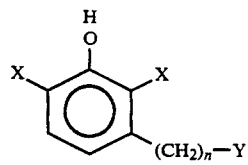

(I)

wherein X is a bromine or chlorine atom, n is 1, 2 or 3, Y is COOR, CONRR', SO$_3$R, SO$_2$NRR' or OR and R and R', independently of one another, are hydrogen atoms or C$_1$-C$_3$-alkyl radicals.

In the 2,6-dihalo-3-alkylphenols according to the present invention, there were, suprisingly, found coupling components which satisfy all requirements. They are stable and insensitive towards autoxidation. The oxidative coupling reaction with the use of the compounds according to the present invention is not influenced by disturbing substances which can be present in body fluids. The resulting colored material is stable, possesses a favourable absorption maximum and a high extinction coefficient. In the test, there are found blank value stability and linearity.

In the compounds according to the present invention, Y is preferably COOR and especially preferably COOH and n is preferably 1.

The present invention also provides a process for the preparation of compounds of the general formula:

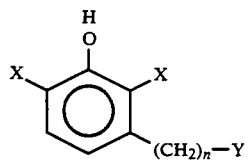

(I)

in which X is a bromine or chlorine atom, n is 1, 2 or 3, Y is COOR, CONRR', SO$_3$R, SO$_2$NRR' or OR and R and R', independently of one another, are hydrogen atoms or C$_1$-C$_3$-alkyl radicals, wherein a compound of the general formula:

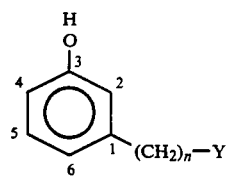

(II)

in which n and Y have the above-given meanings, is reacted by nitration on the 6-position of the aromatic ring to give a compound of the general formula:

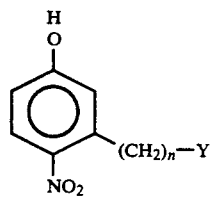

(III)

the compound (III) is reacted by bromination or chlorination in the 2- and 4-position of the aromatic ring to give a compound of the general formula:

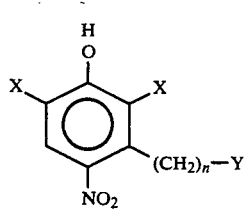

(IV)

in which X is a bromine or chlorine atom and Y and n have the above-given meanings, whereafter the nitro group in the 6-position of the aromatic ring is removed to give a compound of general formula (I).

The first step of the process according to the present invention is a nitration of the starting compound of general formula (II) in the 6-position of the aromatic ring, a compound of general formula (III) thereby being obtained. This nitration can be carried out in known manner by reacting the starting compound with nitric acid, nitrating acid (a mixture of concentrated nitric acid and concentrated sulphuric acid), nitronium tetrafluoroborate or the like.

The second step of the process according to the present invention is a bromination or chlorination of the compound of general formula (III) in the 2- and 4-positions of the aromatic ring to give a compound of general formula (IV). The halogenation of the aromatic ring in the 2- and 4-positions can be carried out in known manner. The bromination of the compound of general formula (III) favourably takes place by reaction thereof with bromine in aqueous alkaline solution. The chlorination favourably takes place by treating the compound of general formula (III) in aqueous solution with hypochlorite.

The last step of the process according to the present invention is the removal of the nitro group in the 6-position of the aromatic ring. This preferably takes place in such a manner that the nitro group in the compound of general formula (IV) is reduced to an amino group, this is converted into a diazonium group and the diazonium group is reductively removed. The reduction of the nitro group to an amino group can take place, for example, in alkaline solution with dithionite or also with tin and hydrochloric acid. The diazotization of the product thereby obtained preferably takes place by reaction with sodium nitrite in the presence of a mineral acid at 0° C. The reduction of the resulting diazonium salt can take place, for example, by heating with hypophosphorous or phosphorous acid, with a salt thereof, with a solution of sodium stanite or with formic acid, it being preferable to heat the diazonium salt with sodium hypophosphite.

In this way, there can be obtained all of the compounds of general formula (I). The preparation of esters and amides of the 2,4-dihalo-3-hydroxyphenylcarboxylic acids and-sulphonic acids takes place from the acids by methods which are known from the literature and are conventional.

The present invention also provides a colorimetric process for the detection of an oxidative coupling reaction, wherein a coupling component is reacted with a developer component in the presence of an oxidation agent to give a colored material, wherein, as coupling component, there is used a compound of the general formula:

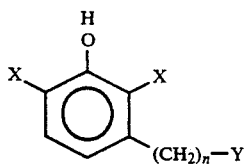

(I')

in which X is a bromine or chlorine atom, n is 1, 2 or 3, Y is COOR, CONRR', SO₃R, SO₂NRR', OR or NRR'R"⊕ and R, R' and R", independently of one another, are hydrogen atoms or $C_1$-$C_3$-alkyl radicals.

It is preferred to use a coupling component in which Y is COOR and especially preferably COOH and n is 1. If Y is NRR' or NRR'R"⊕, the preparation of the coupling component preferably takes place analogously to the process described in published Federal Republic of Germany Patent Specification No. 23 20 967.

In the case of the oxidative coupling reaction, besides the coupling component according to the present invention, a developer component is also necessary which reacts in the presence of an oxidation agent to give a coloured material. As developer components, there can be used the usual aminoantipyrine derivatives, phenylenediamine derivatives or methylbenzthiazolinone hydrazone derivatives, it being preferred to use sulphonated methylbenzthiazolinone hydrazone (SMBTH).

As oxidation agent for the oxidative coupling reaction, it is preferred to use the system hydrogen peroxide/peroxide-activating agent. As peroxide-activating agent, it is preferred to use a peroxidase. Other peroxide-activating agents include, for example, tungstic acid and molybdic acid and the salts thereof or a mixture of an iodide and one of these compounds, as well as iron, copper and cerium ions and vanadic acid. Furthermore, as oxidation agents, there can be used peroxides, such as persulphates or peracetates, as well as periodates, chloramine-T and especially cyanoferric complexes, for example potassium ferricyanide. According to published Federal Republic of Germany Patent Specification No. 33 31 588, oxidases can also be used.

In the case of the process according to the present invention for the detection of an oxidative coupling, there are several principle variants. It is possible to detect either a) the developer component or b) the oxidation agent or a component of the oxidation agent. In both cases, in turn, not only a direct but also an indirect detection is possible, i.e. in a direct detection there can be determined the concentration or amount of the developer component or of the oxidation agent present in the sample, whereas, in an indirect detection, a system is determined by means of which the developer component or the oxidation agent is produced in the sample.

Thus, in a first preferred variant, the present invention includes a process wherein there are detected aromatic amines, which can serve as developer component for the oxidative coupling, or systems which liberate such amines. By systems which liberate aromatic amines are to be understood especially substrates which are accessible to an enzymatic cleavage, whereby the aromatic amine serving as developer component is then formed.

As substrate, it is preferred to use a synthetic peptidamide. By means of cleavage of a peptidamide and the liberation of the developer component involved therewith, there can be detected, for example, the proteolytic enzymes γ-glutamyl transpeptidase, leucine aminopeptidase or thrombin. For the cleavage of thrombin, as substrate there can be used, for example, a synthetic peptidamide tosyl-glycyl-prolylarginine-p-phenylenediamine or also Chromozyme TH ™ commercially available from Boehringer Mannheim G$_m$bH. As oxidation agent for this detection, there can be used, for example, a ferricyanide, hydrogen peroxide/peroxidase, periodate or persulphate, it being preferred to use a ferricyanide or hydrogen peroxide/peroxidase. For the determination of other proteases, there can be used correspondingly appropriate synthetic peptidamides, for example the various commercially available chromozyme derivatives.

In a second preferred variant of the process according to the present invention, the oxidation agent for the oxidative coupling reaction or a component thereof is determined directly. The term "a component of the oxidation agent" refers to the fact that, as oxidation agent, there can be used hydrogen peroxide together with a peroxide-activating substance. Therefore, it is possible to detect not only hydrogen peroxide but also the peroxide-activating substance as components of the oxidation agent. In a direct detection process, the enzymatic activity of peroxidase is preferably determined. For this purpose, hydrogen peroxide, the coupling component according to the present invention, as well as an appropriate developer component, are added to the reaction batch. Preferably, there is detected a peroxidase which is coupled to another polypeptide and especially preferably to an antibody or antibody fragment so that the peroxidase activity can be determined with the help of the coupling component according to the present invention for the quantification of immune tests.

In a further preferred variant of the process according to the present invention, a system is detected which liberates the oxidation agent or a component of the oxidation agent for the oxidative coupling. Hereunder are especially to be understood hydrogen peroxide-producing systems, for example the clinically diagnostically important substrate/substrate oxidase pairs in which the substrate is oxidized in the presence of atmospheric oxygen and hydrogen peroxide is produced. In this way, there can be detected either the substrate or the substrate oxidase, depending upon which component is added to the reagent. As example of substrate/substrate oxidase pairs, there are to be mentioned the following hydrogen peroxide-forming systems: glucose/glucose oxidase, galactose/galactose oxidase, L-amino acid/L-amino acid oxidase, cholesterol/cholesterol oxidase, uric acid/uricase, sarcosine/sarcosine oxidase, glycerol/glycerol oxidase, glycerol phosphate/glycerol phosphate oxidase and pyruvate/pyruvate oxidase.

The detection process according to the present invention can be carried out not only in a cuvette but also on dry reagent carriers. The quantification of the oxidative coupling reaction can thereby take place by means of photometers by way of a transmission measurement, with remission photometers by way of remission measurement or with the help of comparative colors a visual comparison is also possible.

The present invention is also concerned with the use of a compound of the above-given general formula (I') as coupling component for the detection of an oxidative coupling reaction wherein the coupling component is reacted with a developer component in the presence of an oxidation agent to give a colored material. The coupling components according to the present invention are preferably used for the detection of hydrogen peroxide or of a hydrogen peroxide-liberating system or for the detection of peroxidase or of another peroxide-activating agent or for the detection of an aromatic amine which is suitable as developer component or of a system which can liberate such an amine.

Furthermore, the present invention provides a reagent for the detection of an oxidative coupling reaction, wherein a coupling component is reacted with a developer component in the presence of an oxidation agent to give a coloured material, said reagent comprising a compound of general formula (I') as coupling component, an appropriate buffer and optionally wetting agents, activators or other known adjuvants.

With the reagent according to the present invention, test systems can be produced which are measured in a cuvette. For this purpose, a coupling component according to the present invention, together with the substances necessary for the particular parameter detection (enzymes or other reagents), the buffer and possibly wetting agents, activators and other adjuvants are mixed as powder and pressed to give tablets or preferably dissolved in water and again dried or lyophilised. The reagent mixture thus obtained is, before use, dissolved in water or some other suitable solvent and, in this way, a reagent solution is made available. After mixing of the sample (substrate solution, enzyme solution, serum or plasma) with an aliquot of the reagent solution or reagent mixture, the color of the colored material resulting due to the oxidative coupling is measured with the use of a photometer. Via the molar extinction coefficient and the added reagent or sample volume, there is calculated the particular concentration of the parameter to be detected. Not only kinetic but also end point measurements are thereby possible.

In the same way, the coupling components according to the present invention, in combination with the developer component capable of oxidation, together with peroxidase, the reagents or enzymes necessary for the parameter detection in question, the buffer system, optionally wetting agents and activators, as well as other adjuvants, can be impregnated on to absorbent reagent carriers, for example papers, fleece of the like. For this purpose, there can be prepared one or more impregnation solutions in the form of aqueous or organic or mixed solutions as is necessary according to the solubility of the reagents and/or adjuvants. Absorbent or swellable carriers, preferably filter paper or absorbent glass or synthetic material fleece, are impregnated or sprayed with these solutions, followed by drying. The reagent carriers produced in this manner can be used as rapid diagnostics for the direct determination of component materials of liquids, for example body fluids, such as blood, urine or saliva, or of foodstuffs, such as fruit juices, milk or the like. The liquid to be determined is thereby brought into contact with the reagent carrier. A semiquantitative determination can take place by comparison of the thus resulting color with a reference color. A quantitative evaluation preferably takes place by remission photometry. The remission photometric evaluation can be carried out especially well when the indicator, together with the other necessary reagents and adjuvants and a film-forming synthetic material, is worked up to give a reagent film, for example according to Federal Republic of Germany Patent Specification No. C-15 98 153.

Buffer systems appropriate for the reagent or process according to the present invention preferably have a pH value of from 6 to 10 and especially preferably of from 6.5 to 7.5. Phosphate, citrate, borate or GOOD buffers with alkali metal or ammonium counterions are most frequently used. However, other systems can also be used. Wetting agents are especially anionic and cationic wetting agents which can enter into ionic exchange actions with the compounds according to the present invention. However, nonionic wetting agents which can activate enzymes can also be used. Sodium lauryl sulphate, dioctyl sodium sulphosuccinate and alkylaryl polyether alcohols are preferred. As activators, there are to be used those known for the substrate reactions in question. The oxidative coupling itself proceeds so quickly that and additional activation does not appear to be necessary. As other adjuvants, there can be used conventional thickeners, emulsifiers, optical brighteners, contrast agents and the like, if desired, such as are known in corresponding tests with different coupling components.

The coupling reaction usually takes place at ambient temperature but it can also readily be carried out at a higher temperature, for example at 37° C., when this is desirable for the reaction velocity of, for example, a preceding enzymatic reaction. For the reactions which usually occur with substrates, for example enzymes, the following concentrations of the test solution have proved to be useful:

coupling component: 0.05 to 100 mmole/liter, preferably 0.1 to 3 mmole/liter,
developer component: 0.05 to 50 mmole/liter, preferably 0.1 to 1 mmole/liter
buffer: 0.05 to 1 mole/liter, preferably 0.1 to 0.5 mole/liter
wetting agent: 0 to 1 mole/liter, preferably 0.05 to 0.1 mole/liter.

If peroxidase is added to the test reagent, then this preferably takes place at a concentration of from 1.0 to 5000 kU/liter. If hydrogen peroxide or a hydrogen peroxide-producing substrate or a substrate oxidase is added to the reagent, then this preferably takes place at a concentration of from 0.1 to 10 mmole/liter. Other adjuvants can be present in a concentration of from 0 to 5 mole/liter.

The mentioned concentration ranges are to be so understood that the lower ranges are in each case preferred for photometric tests in a cuvette and the upper ranges for rapid tests or for tests on solid carriers.

For the detection of enzymes acting as amidases, in the above-given description, the developer components are replaced by a corresponding amount of the peptidamide substrate and, instead of hydrogen peroxide, there is possibly used a corresponding amount of some other oxidation agent, for example potassium ferricyanide.

The following Examples are given for the purpose of illustrating the present invention:

EXAMPLE 1

Preparation of 2,4-dibromo-3-hydroxyphenylactic acid a) 3-Hydroxy-6-nitrophenylacetic acid 15.2 g. (100 mmole) 3-hydroxyphenylacetic acid are suspended in 15 ml. water and, while cooling, 17.5 ml. of a 65% nitric acid slowly added dropwise thereto. The reaction mixture is subsequently stirred for 1 hour at ambient temperature and then poured on to ice. The precipitate obtained is filtered off and washed with a little ethyl acetate. Further product is recovered from the filtrate. This is adjusted to pH 1 and washed with chloroform. The pH is subsequently adjusted to 5.5, followed by shaking out several times with ethyl acetate. The combined ethyl acetate phases are washed with water and concentrated. After cooling, a precipitate is obtained which is filtered off and washed with a little ethyl acetate. Yield 6.8 g. (34% of theory). M.p. 194° C.

TLC: $R_f=0.42$ (silica gel; chloroform/methanol 6:1 v/v+1% glacial acetic acid).

b) 2,4-Dibromo-3-hydroxy-6-nitrophenylacetic acid 10 g. (50 mmole) of the product from 1a) are dissolved in 100 ml. water and 50 ml. 2N aqueous sodium hydroxide solution and then 6 ml. bromine are added dropwise thereto within the course of 20 minutes. After a short time, a precipitate is obtained which is filtered off and washed with water. Yield 16.5 g. (92% of theory).

TLC: $R_f=0.4$ (silica gel; chloroform/methanol 6:1 v/v+1% glacial acetic acid).

c) 6-Amino-2,4-dibromo-3-hydroxyphenylacetic acid 16.2 g. (46 mmole) of the product from 1b) are taken up in 140 ml. water and mixed with 277 ml. 2N aqueous sodium hydroxide solution. With cooling with ice, 57.6 g. sodium hydrosulphite are added portionwise thereto, followed by acidification and shaking out with ethyl acetate. The combined ethyl acetate phases are washed with water and dried over anhydrous sodium sulphate. After removal of the solvent, the desired product remains behind. Yield 8 g. (54% of theory).

TLC: $R_f=0.31$ (silica gel; chloroform/methanol 1:1 v/v+1% glacial acetic acid).

d) 2,4-Dibromo-3-hydroxyphenylacetic acid 8 g. (24.6 mmole) of the product from 1c) are taken up in 155 ml. 10% sulphuric acid and, while cooling, a solution of 7.5 g. sodium nitrite in 30 ml. water added dropwise thereto. The resulting suspension is further stirred for 20 minutes and then added portionwise to a solution, heated to 70° C., of 38 g. sodium hypophosphite in 15.4 ml. water. Subsequently, the reaction mixture is left for 1 hour at 70° C. and then cooled. The precipitate obtained is filtered off and purified by silica gel chromatography (elution agent: ethyl acetate/petroleum ether 6:2 v/v). The isolated product is subsequently recrystallised from ethyl acetate/hexane. Yield: 1.6 g. (22% of theory): m.p. 186° C.

TLC: $R_f=0.27$ (silica gel; ethyl acetate/petroleum ether 6:1 v/v).

EXAMPLE 2

Preparation of 2,4-dichloro-3-hydroxyphenylacetic acid a) 2,4-Dichloro-3-hydroxy-6-nitrophenylacetic acid 10.8 g. (55 mmole) of the product from Example 1a) are dissolved in 330 ml. water and mixed with 180 ml. sodium hypochlorite solution. After stirring for 1 hour, the reaction mixture is acidified with concentrated hydrochloric acid to pH 1. The resultant precipitate is filtered off and washed with hydrochloric acid and water. Further product can be isolated from the mother liquor by shaking out with ethyl acetate. Yield 10.4 g. (71% of theory).

TLC: $R_f=0.4$ (silica gel; chloroform/methanol 6:1 v/v+1% glacial acetic acid).

b) 6-Amino-2,4-dichloro-3-hydroxyphenylacetic acid

This is obtained from 9.5 g. (36 mmole) of the product from 2a), 47 g. sodium dithionite, 66 ml. water and 137 ml. 2N aqueous sodium hydroxide solution analogously to Example 1c), Yield 6.6 g. (78% of theory).

TLC: $R_f=0.38$ (silica gel; chloroform/methanol 6:1 v/v+1% glacial acetic acid).

c) 2,4-Dichloro-3-hydroxyphenylacetic acid

This is obtained from 7 g. (30 mmole) of the product from 2b), 190 ml. 10% sulphuric acid, 5.3 g. sodium nitrite, 60 g. sodium hypophosphite analogously to Example 1d). Column chromatography is carried out with ethyl acetate/petroleum ether (1:1 v/v). Yield TLC: $R_f=0.44$ (silica gel; ethyl acetate/petroleum ether 1:1 v/v).

EXAMPLE 3

Determination of creatinine

Carrying out of the test

Enzymatic creatinine determination via creatinine iminohydrolase, N-methylhydantoinase, N-carbamoyl-sarcosine amidohydrolase and sarcosine oxidase (cf. J. Siedel et al., Analytical Letters, 21, 1009–1017/1988) hereby incorporated by reference using the Hitachi automatic analyser 704.

350 μl. of reagent 1 (containing 15 U/liter creatinine iminohydrolase, 0.5 U/ml. N-methylhydantoinase, 5 U/ml. sarcosine oxidase and 3 U/ml. peroxidase, as well as the particular investigated phenolic coupler in 100 mmole/liter TRIS/HCl, pH 7.9) are pipetted into 7 μl. of serum sample. After a pre-incubation for 5 minutes, there are pipetted thereto 70 μl. of reagent 2 (containing 15 U/ml. carbamoylsarcosine amidohydrolase, 0.9 mmole/liter MBTH-S (3-methylbenzo-(2'-sulpho)-thiazolinone hydrazone), 30 mmol/liter ATP in 100 mmol/liter TRIS/HCl, pH 7.9) and the extinction increase is measured at 546 nm from the 6th to the 10th minute. As phenolic color coupler, there is, in each case, used the amount of 2,4-dibromo-3-hydroxyphenyl acetic acid optimised to maximum sensitivity (2.4 mmole/liter).

Reagent Compositions

Reagent 1

100 mmole/liter TRIS/HCl, pH 7.9 (ambient temperature)
200 mmole/liter potassium chloride
5 mmole/liter magnesium chloride
10 mmole/liter ammonium chloride
10 μmole/liter potassium ferricyanide
15 U/ml. Creatinine iminohydrolase
0.5 U/ml. 1-methylhydantoinase
5 U/ml. sarcosine oxidase
10 U/ml. ascorbate oxidase
3 U/ml. peroxidase
2.4 mmol/liter 2,4-dibromo-3-hydroxyphenylacetic acid (2 mmole/liter in the test).

Reagent 2

100 mmole/liter TRIS/HCl, pH 7.9 (ambient temperature)
30 mmole/liter ATP
15 U/ml. carbamoylsarcosine hydrolase
0.9 mmole/liter MBTH-S (0.15 mmole/liter in the test)

Carrying out of the test

Measurement on a Hitachi 704 photometer
350 µl. Reagent 1
7 µl. sample
incubation for 5 minutes
70 µl. Reagent 2
measurement from the 6th to the 10th minute
measurement temperature: 37° C.
measurement wavelength: 546 nm
reference wavelength: 700 nm.

Disturbances in an enzymatic creatinine test

An oxidative coupling reaction was carried out for the determination of creatine in serum. As coupling components, there were compared 2,4,6-tribromo-3-hydroxybenzoic acid (according to published European Patent Specification A-0,108,526) and 2,4-dibromo-3-hydroxyphenylacetic acid (according to Example 1 of the present invention). Methylbenzthiazoline hydrazone sulphonate was used as developer component.

The serum used in the test was made up with bilirubin, haemoglobin, ascorbic acid, dobesilate calcium and methyldopa. The following Table I shows that the creatinine finding again was, in each case, better than in the case of using the known tribromohydroxybenzoic acid.

TABLE I

Creatinine finding again (%) in made-up human sera

| disturbance (additive) | tribromohydroxy-benzoic acid (according to EP-A-0,108,526) | dibromohydroxy-phenylacetic acid (according to the present invention |
|---|---|---|
| bilirubin, 25 mg/dl | 64.7 | 92.1 |
| haemolysis, 300 mg/dl Hb | 103.8 | 101.8 |
| dobesilate calcium, 50 mg/dl | 95.8 | 96.5 |
| methyldopa, 20 mg/l. | 89.7 | 96.3 |
| ascorbic acid, 30 mg/dl | 97.2 | 100.0 |

EXAMPLE 4

Preparation of 2,6-dibromo-3-hydroxyethylphenol a) 3-Hydroxyethyl-4-nitrophenol

This was obtained analogously to Example 1a) from 17.5 g. 2-(m-hydroxyphenyl)-ethanol and 42 ml. 40% nitric acid. Yield 6.9 g. (30% of theory); m.p. 167° C.

TLC: $R_f=0.26$ (silica gel; toluene/ethyl acetate 1:4 v/v).

b) 2,6-Dibromo-3-hydroxyethyl-4-nitrophenol

This was obtained analogously to Example 1b) from 10 g. of the product from 4a), 110 ml. water, 50 ml. 2N aqueous sodium hydroxide solution and 7.2 ml. bromine.

Yield 17.1 g. (93% of theory); m.p. 137° C.

TLC: $R_f=0.1$ (silica gel, toluene/ethyl acetate 1:4 v/v).

c) 4-Amino-2,6-dibromo-3-hydroxyethylphenol

This was obtained analogously to Example 1c) from 21.8 g. of the product from 4b), 200 ml. water, 388 ml. 2N aqueous sodium hydroxide solution and 81 g. sodium hydrosulphite. Yield 15.1 g. (76% of theory).

TLC: $R_f=0.83$ (silica gel; chloroform/methanol 1:1 v/v).

d) 2,6-Dibromo-3-hydroxyethylphenol

This was obtained analogously to Example 1d) from 15.1 g. of the product from 4c), 300 ml. 10% sulphuric acid, 7.5 g. sodium nitrite and 74 g. sodium hypophosphite. The precipitate obtained was recrystallised from water. Yield 500 mg.

TLC: $R_f=0.68$ (silica gel; toluene/ethyl acetate 1:3 v/v).

EXAMPLE 5

Preparation of 2,4-dibromo-3-hydroxyphenylpropionic acid 5a) 3-Hydroxyphenylpropionic acid 15 g. 3-Hydroxycinnamic acid was dissolved in 300 ml. water/ethanol (1:1 v/v) and hydrogenated in the presence of 0.75 g. palladium/active carbon until no further take-up of hydrogen was observed. After filtering off the catalyst, the solvent was stripped off. Yield 14.7% (97% of theory).

TLC: $R_f=0.63$ (silica gel; chloroform/methanol 4:1 v/v).

The following synthesis stages were prepared analogously to the previously described Examples. The data are summarized in the following Table.

5b) 3-hydroxy-6-nitrophenylpropionic acid analogously to Example 1a)

5c) 2,4-dibromo-3-hydroxy-6-nitrophenylpropionic acid analogously to Example 1b)

5d) 6-amino-2,4-dibromo-3-hydroxyphenylpropionic acid analogously to Example 1c)

5e) 2,4-dibromo-3-hydroxyphenylpropionic acid analogously to Example 1d)

TABLE

| preparation | yield (%) | TLC = $R_f$ (silica gel) | elution agent |
|---|---|---|---|
| 5b) | 19 | 0.53 | chloroform/methanol 7:1 v/v + 1% acetic acid |
| 5c) | 50 | 0.15 | chloroform/methanol 4:1 v/v |
| 5d) | 49 | 0.23 | chloroform/methanol 4:1 v/v |
| 5e) | 10 | 0.28 | ethyl acetate/petroleum ether 6:1 v/v |

EXAMPLE 6

2,4-Dibromo-3-hydroxyphenyl-ethylsulphonic acid 6a) 3-Hydroxyphenyl-ethylenesulphonic acid The preparation took place from 3-hydroxybenzaldehyde and sulphoacetic acid by a Knoevenagel condensation analogously to G. Jones, Org. Reaction, 15, 204/1967 hereby incorporated by reference.

The following synthesis stages were prepared analogously to the previously described Examples:

6b) 3-hydroxyphenyl-ethylsulphonic acid analogously to Example 5a)

6c) 3-hydroxy-6-nitrophenyl-ethylsulphonic acid analogously to Example 1a)

6d) 2,4-dibromo-3-hydroxy-6-nitrophenyl-ethylsulphonic acid analogously to Example 1b)

6e) 6-amino-2,4-dibromo-3-hydroxyphenyl-ethylsulphonic acid analogously to Example 1c)

6f) 2,4-dibromo-3-hydroxyphenyl-ethylsulphonic acid analogously to Example 1d).

It will be understood that the specification and examples are illustrative but not limitative of the present invention and that other embodiments within the spirit and scope of the invention will suggest themselves to those skilled in the art.

We claim:

1. Compounds of the formula:

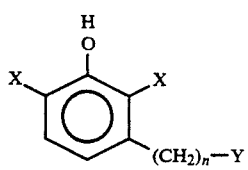

(I)

wherein X is bromine or chlorine, n is 1, 2 or 3, Y is COOR, CONRR', SO$_3$R, SO$_2$NRR' or OR and R and R', independently of one another, are hydrogen or C$_1$–C$_3$-alkyl.

2. Compounds according to claim 1 wherein Y is COOR.

3. Compounds according to claim 1 or 2 wherein n is 1.

4. Process for the preparation of compounds of the formula:

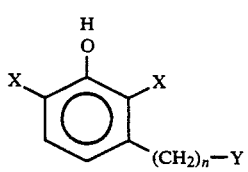

(I)

wherein X is bromine or chlorine, n is 1, 2 or 3, Y is COOR, CONRR', SO$_3$R, SO$_2$NRR' or OR and R and R', independently of one another, are hydrogen or C$_1$–C$_3$-alkyl, comprising reacting a compound of the formula:

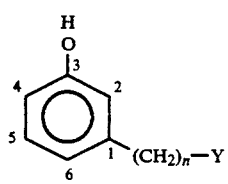

(II)

in which n and Y have the above-given meanings by nitration in the 6-position of the aromatic ring to give a compound of the formula:

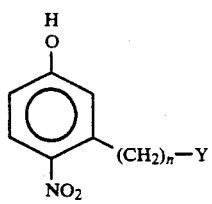

(III)

in which n and Y have the above-given meanings, subsequently reacting the compound (III) by bromination or chlorination in the 2- and 4-position of the aromatic ring to give a compound of the formula:

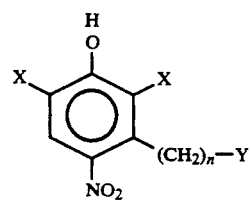

(IV)

is which n and Y have the above-given meanings and X is bromine or chlorine, and removing the nitro group in the 6-position of the aromatic ring to give the end product (I).

5. Process according to claim 4, wherein the nitro group in the compound of general formula (IV) is reduced to an amino group, the amino group is converted into a diazonium group and subsequently the diazonium group is removed reductively.

6. Compounds of formula (I) according to claim 1, as prepared by the process according to any one of claims 4 or 5.

7. Colorimetric process for the detection of an oxidative coupling reaction in which a coupling component is reacted with a developer component in the presence of an oxidation agent to give a colored material, wherein the coupling component, is a compound of the formula:

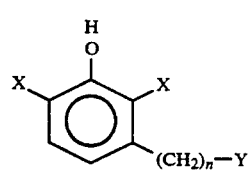

(I')

in which X is bromine or chlorine, n is 1, 2 or 3, Y is COOR, CONRR', SO$_3$R, SO$_2$NRR', OR, NRR' or NRR'R''+ and R, R' and R'', independently of one another, are hydrogen or C$_1$–C$_3$-alkyls.

8. Process according to claim 7, wherein the oxidation agent is selected from the group consisting of hydrogen peroxide/peroxide-activating agent, periodate, persulphate, peracetate, perborate, chloramine T and a cyanoferric complex.

9. Process of claim 8, wherein the peroxide-activating agent is peroxidase.

10. Process of any one of claims 7 to 9 wherein the developer component is selected from the group consisting of an aminoantipyrine derivative, a phenylenediamine derivative and a methylbenzthiazolinone hydrazone derivative.

11. Process of any one of claims 7 or 9 wherein the developer component of the oxidative coupling reaction is detected directly or indirectly.

12. Process of claim 11, wherein an aromatic amine is detected as the developer component for the oxidative coupling or a system which can liberate such an aromatic amine.

13. Process according to claim 12, wherein enzymatic cleavage of a substrate liberates the aromatic amine.

14. Process according to claim 13, wherein the substrate is a synthetic peptidamide.

15. Process according to claim 13 or 14, wherein the enzyme γ-glutamyltranspeptidase, leucine aminopeptidase or thrombin is detected by cleavage of a peptidamide.

16. Process of any one of claims 7 to 9 wherein the oxidation agent of the oxidative coupling reaction or a component thereof is detected directly or indirectly.

17. Process according to claim 16, wherein hydrogen peroxide or a hydrogen peroxide-liberating system is detected.

18. Process according to claim 17, wherein hydrogen peroxide is liberated by catalytic oxidation of a substrate in order to detect the substrate or the substrate oxidase catalytically oxidizing the substrate.

19. Process according to claim 18, wherein a substance occurring in an organism is detected as the substrate.

20. Process according to claim 19, wherein the substance occurring in the organism is selected from the group consisting of glucose, galactose, an L-amino acid, cholesterol, uric acid, sarcosine, glycerol, glycerol phosphate and pyruvate.

21. Process according to claim 18, wherein a substrate oxidase is detected.

22. Process according to claim 21, wherein the substrate oxidase is selected from the group consisting of glucose oxidase, galactose oxidase, an L-amino acid oxidase, cholesterol oxidase, uricase, glycerol oxidase, glycerol phosphate oxidase and pyruvate oxidase.

23. Process according to claim 16, wherein peroxidase or another peroxide-activating agent is detected.

24. Process according to claim 23, wherein peroxidase coupled to a polypeptide is detected.

25. Process according to claim 24, wherein the polypeptide is an antibody or an antibody fragment.

26. Reagent for the detection of an oxidative coupling reaction in which a coupling component is reacted with a developer component in the presence of an oxidation agent to give a colored material, wherein the reagent contains a compound of the formula:

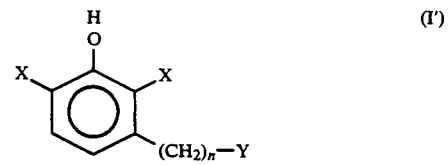

(I')

as a coupling component wherein X is bromine or chlorine, n is 1, 2 or 3, Y is COOR, CONRR', SO$_3$R, SO$_2$NNR', OR, NNR' or NNR'R''+ and R, R' and R'', independently of one another, are hydrogen or C$_1$–C$_3$-alkyl, an appropriate buffer and optionally wetting agents, activators or other adjuvants.

27. Reagent according to claim 26, wherein the coupling component is present in the test solution in a concentration of from 0.05 to 100 mmole/liter.

28. Reagent according to claim 27, wherein the coupling component is present in the test solution in a concentration of from 0.1 to 3 mmole/liter.

29. An absorbent reagent carrier having impregnated thereon the reagent of claim 26 together with peroxidase and enzymes for determination of an oxidative coupling reaction.

30. A test kit comprising the reagent of claim 26 together with peroxidase and enzymes for determination of an oxidative coupling reaction.

31. The compound of claim 1 designated 2,4-dibromo-3-hydroxyphenylacetic acid.

32. The compound of claim 1 designated 2,4-dichloro-3-hydroxyphenylacetic acid.

33. The compound of claim 1 designated 2,6-dibromo-3-hydroxyethylphenol.

34. The compound of claim 1 designated 2,4-dibromo-3-hydroxyphenylpropionic acid.

35. The compound of claim 1 designated 2,4-dibromo-3-hydroxyphenylethylsulphonic acid.

36. The process of claim 7 wherein the coupling compound is 2,4-dibromo-3-hydroxyphenylacetic acid.

37. The process of claim 7 wherein the coupling compound is 2,6-dibromo-3-hydroxyethylphenol.

38. The process of claim 7 wherein the coupling compound is 2,4-dibromo-3-hydroxyphenylethylpropionic acid.

39. The process of claim 7 wherein the coupling compound is 2,4-dibromo-3-hydroxyphenylethylsulphonic acid.

* * * * *